United States Patent
Murai et al.

(10) Patent No.: US 6,217,875 B1
(45) Date of Patent: Apr. 17, 2001

(54) INHIBITORS OF LIPOXYGENASE

(75) Inventors: Hiromichi Murai, Ichinomiya; Tadashi Okada, Gifu-ken; Hiroyo Yamamoto, Ichinomiya, all of (JP)

(73) Assignee: Oryza Oil & Fat Chemical Co., Ltd., Aichi-Ken (JP)

( * ) Notice: Subject to any disclaimer, the term of this patent is extended or adjusted under 35 U.S.C. 154(b) by 0 days.

(21) Appl. No.: 09/053,064

(22) Filed: Apr. 1, 1998

(30) Foreign Application Priority Data

Apr. 23, 1997 (JP) .................................................. 9-105959

(51) Int. Cl.$^7$ .................................................. A61K 35/78
(52) U.S. Cl. .......................................................... 424/195.1
(58) Field of Search .......................................... 424/195.1

(56) References Cited

U.S. PATENT DOCUMENTS

| | | | |
|---|---|---|---|
| 4,329,361 | * 5/1982 | Zenk et al. | 424/317 |
| 4,708,964 | * 11/1987 | Allen | 514/533 |
| 5,043,323 | * 8/1991 | Bombardelli et al. | 514/25 |
| 5,858,371 | * 1/1999 | Singh et al. | 424/195.1 |

FOREIGN PATENT DOCUMENTS

| | | | |
|---|---|---|---|
| 59-005110 | * 1/1984 | (JP) | . |
| WO 94/27563 | * 12/1994 | (WO) | . |

OTHER PUBLICATIONS

Gerritsen, M.E., et al., Flavoniods Inhibit Cytokine–Induced Endothelial Cell Adhesion Protein Gene Expression, Amer. J. of Pathology, vol. 147(2), p. 278–292, Aug. 1985.
Robak, J. et al., Screening of the Influence of Flavonoids on Liboxygenase and Cyclooxygenase Activity, as well as on Nonenzymic Lipid Oxidation, Pol. J. Pharmacol. Pharm., vol. 40(5), p. 451–458, 1988.
Zarga, M.A. et al., Chemical Constituents of Artemisia Arborescens and the Effect of the Aqueous Extract of Rat Isolated Smooth Muscle, Planta Med., vol. 61(3), p. 242–245, 1995.
Lyckander, I.M. et al., Lipophilic Flavonoids from Orthosiphon Spicatus as Inhibitors of 15–Lipoxygenase, Acta. Pharm. Nord., vol. 4(3), p. 159–166, 1992.
Hsieh, R.J. et al., Relative Inhibitory Potencies of Flavonoids on 12–Lipoxygenase of Fish Gill, Lipids, vol. 23(4), p. 322–326, 1988.
Flamini, G. et al., Phenolic Compounds from Santolina Pinnata, Planta Med., vol. 60(1), p. 97, 1994.
Biswas, K.M. et al., Isolation of Chrysoeriol 7–O–β–D – Glucopyrano–Sidyl (2→1)–D–Apiofuranoside from the Leaves of Dalbergia Volubilis, Indian J. Chem., vol. 15B(4), p. 396–397, Apr. 1977.

Williams, C.A. et al., A Biologically Active Lipophilic Flavonol from Tanacetum Parthenium, Phytochemistry, vol. 38(1), p. 267–270, 1995.
Baumann, J. et al., Flavonoids and Related Compounds as Inhibitors of Arachidonic Acid Peroxidation, Prostaglandins, vol. 20(4), p. 627–639, Oct. 1980.
Welton, A.F. et al., Effect of Flovonoids on Arachidonic Acid Metabolism, Prog. Clin. Biol. Res., vol. 213, p. 231–242, 1986.
Silvan, A.M. et al., Effects of Compounds Extracted from Santolina Oblongifolia on $TXB_2$ Release in Human Platelets, Inflammopharmacology, vol. 6(3), p. 255–263, 1998.
Ishikura, Agric. Biol. Chem. 45(8): 1855–1860 (1981).*
Gerritsen, M.E. et al., Amer. J. of Pathology, vol. 147(2), p. 278–292, Aug. 1995.*
Robak, J. et al., Pol. J. Pharmacol. Pharm., vol. 40(5), p. 451–458, 1988.*
Zarga, M.A. et al., Planta Med., vol. 61(3), p. 242–245, 1995.*
Lyckander, I.M.et al., Acta. Pharm. Nord., vol. 4(3), p. 159–166, 1992.*
Hsieh, R.J. et al., Lipids, vol. 23(4), p. 322–326, 1988.*
Flamini, G. et al., Planta Med., vol. 60(1), p. 97, 1994.*
Biswas, K.M. et al., Indian J. Chem., vol. 15B(4), p. 396–397, Apr. 1977.*
Williams, C.A. et al., Phytochemistry, vol. 38(1), p. 267–270, 1995.*
Baumann, J. et al., Prostaglandins, vol. 20(4), p. 627–639, Oct. 1980.*
Welton, A.F. et al., Prog. Clin. Biol. Res., vol. 213, p. 231–242, 1986.*
Silvan, A.M.et al., Inflammopharmacology, vol. 6(3), p. 255–263, 1998.*
Yamamoto, Hiroyo et al., Inhibitory Activity of Arachidonic Acid Metabolic Enzyme (In Vitro), Apr. 2, 1997, (Inventor's paper in Japanese with translation.

* cited by examiner

*Primary Examiner*—Jean C. Witz
(74) *Attorney, Agent, or Firm*—Lowe Hauptman Gilman & Berner, LLP

(57) ABSTRACT

Novel inhibitors of the enzyme action of lipoxygenase, especially 5-lipoxygenase and 12-lipoxygenase that are derived from the extraction of the seeds of the perilla (crispa) or perilla (frutescens) plant. These inhibitors are suitably extracted from these seeds using alcohol, preferably ethanol, to form an extract or more preferably to further extract the alcoholic extract with ethyl acetate and water to partition the active inhibitors to the ethyl acetate. The particularly preferred inhibitors are luteolin and chrysoeriol.

24 Claims, 8 Drawing Sheets

(Fig. 2)
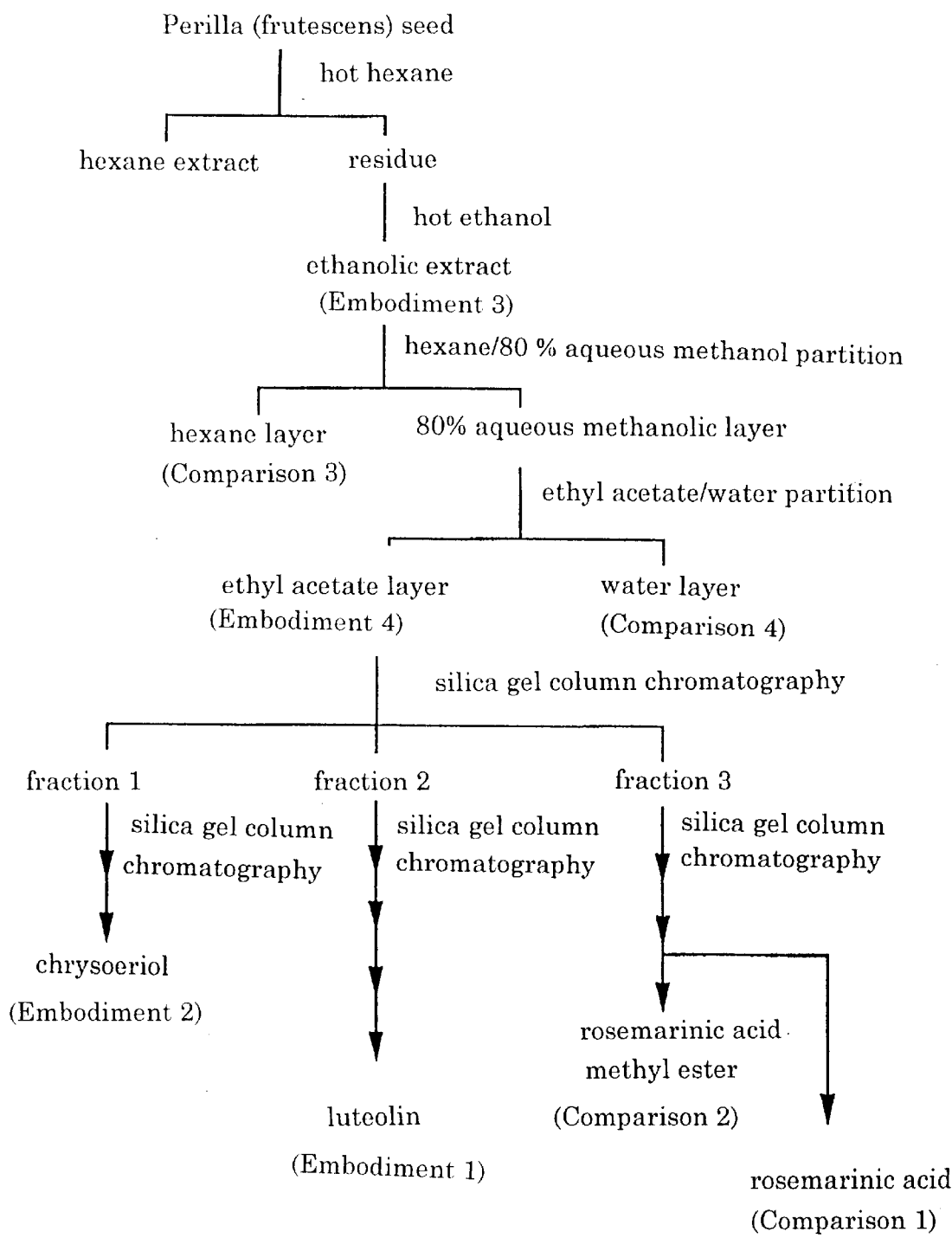

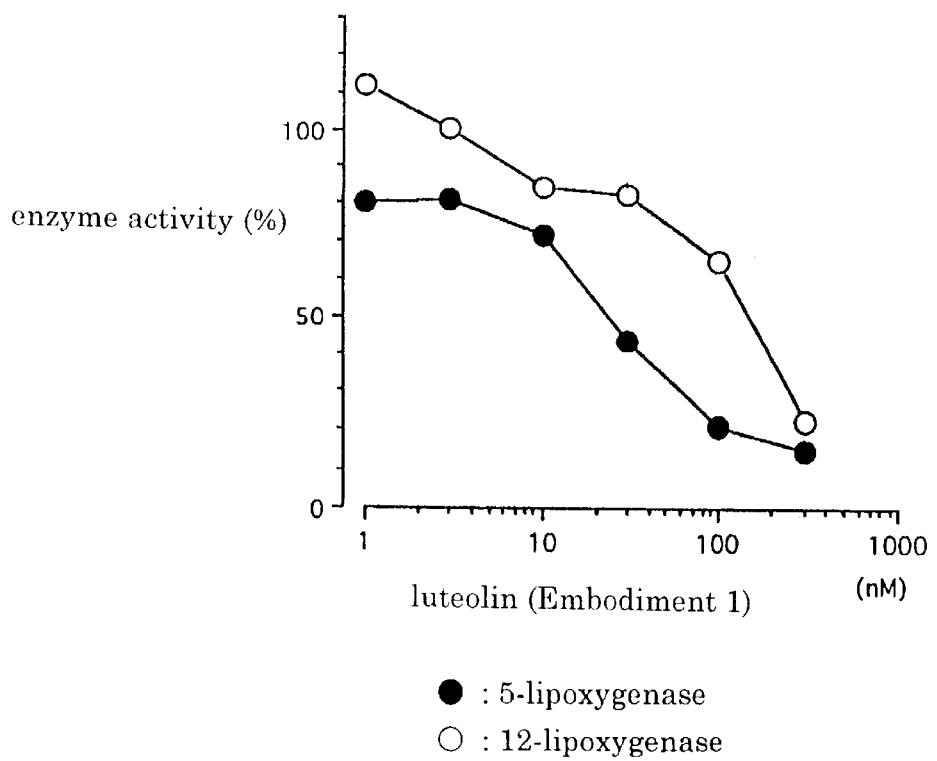
(Fig. 3)
● : 5-lipoxygenase
○ : 12-lipoxygenase (Fig. 4)
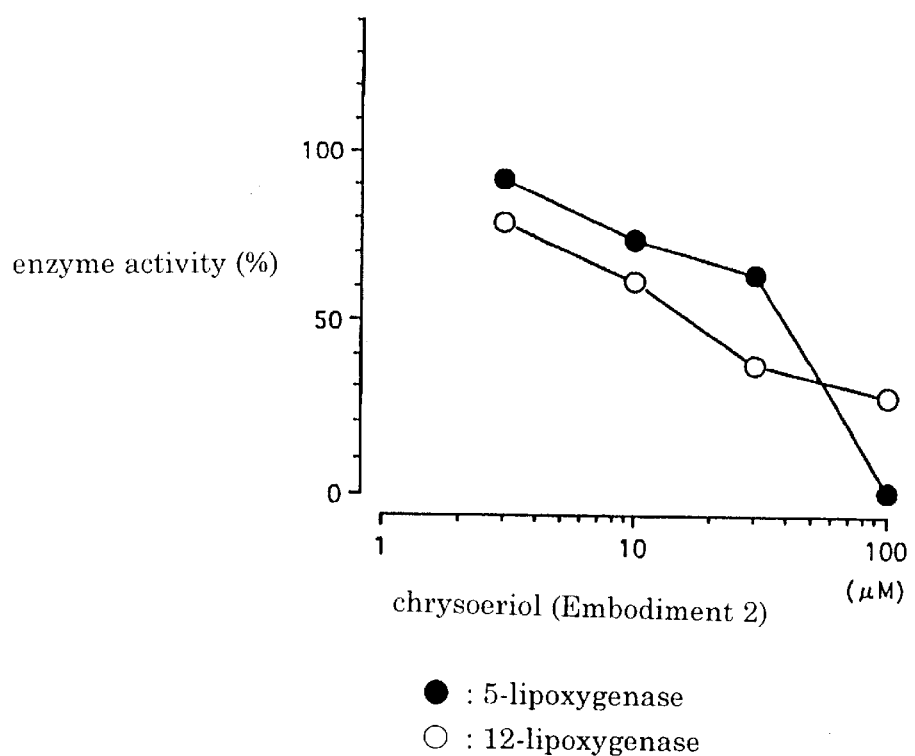
chrysoeriol (Embodiment 2)
● : 5-lipoxygenase
○ : 12-lipoxygenase (Fig. 5)
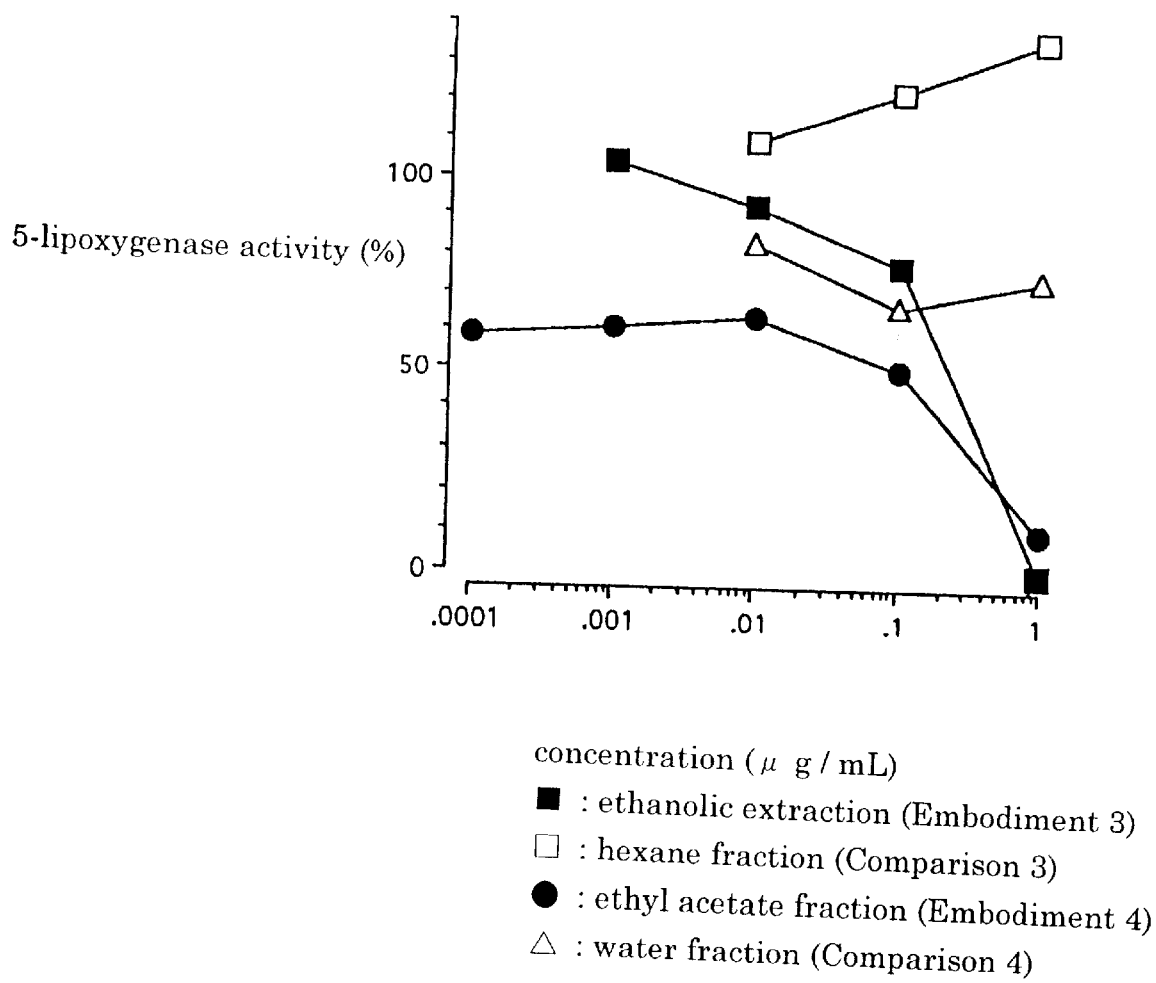

(Fig. 6)
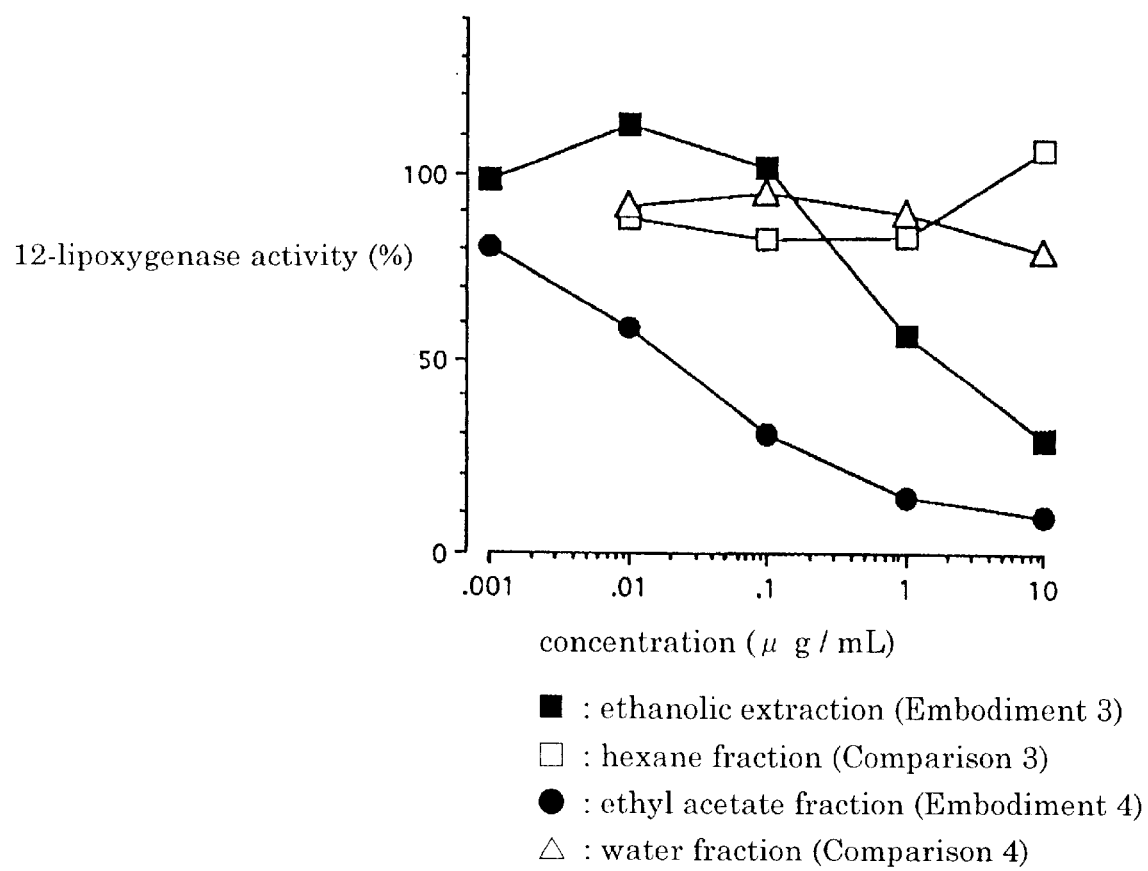
■ : ethanolic extraction (Embodiment 3)
□ : hexane fraction (Comparison 3)
● : ethyl acetate fraction (Embodiment 4)
△ : water fraction (Comparison 4)

(Fig. 7)
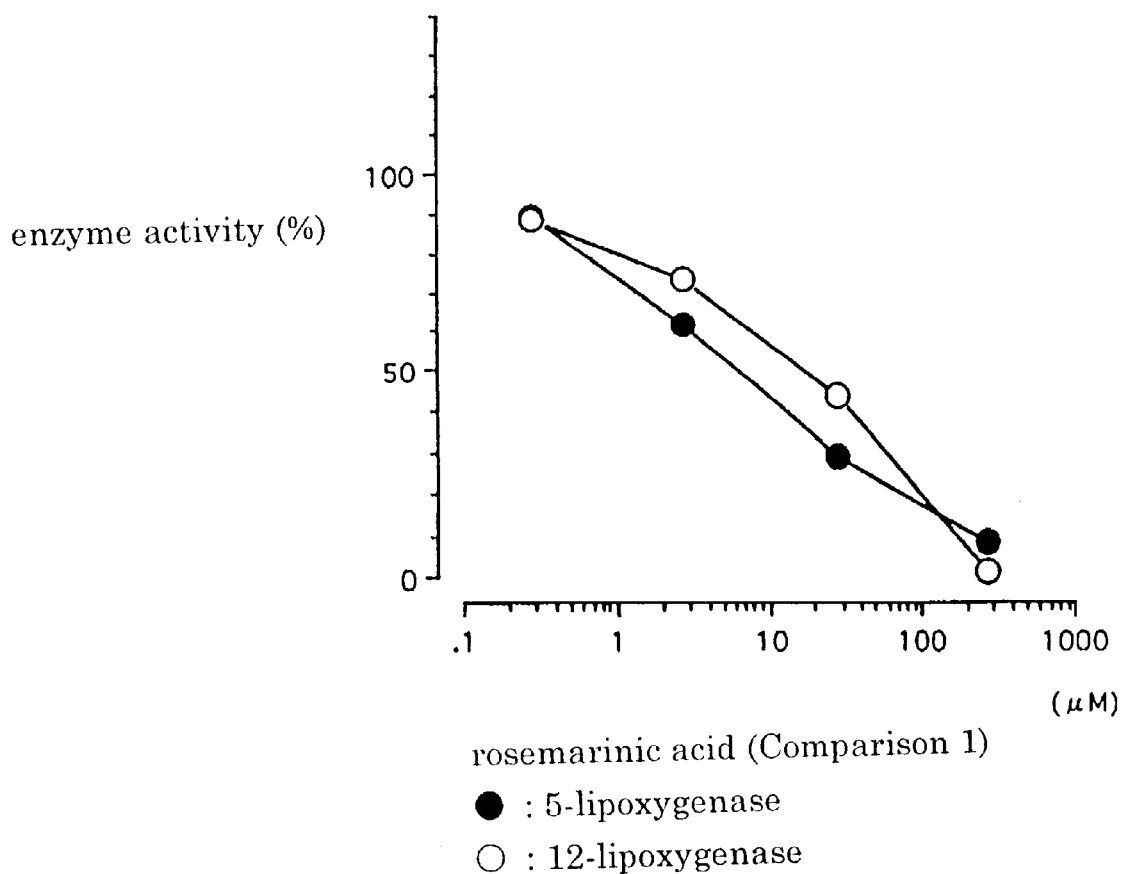
rosemarinic acid (Comparison 1)
● : 5-lipoxygenase
○ : 12-lipoxygenase (Fig. 8)
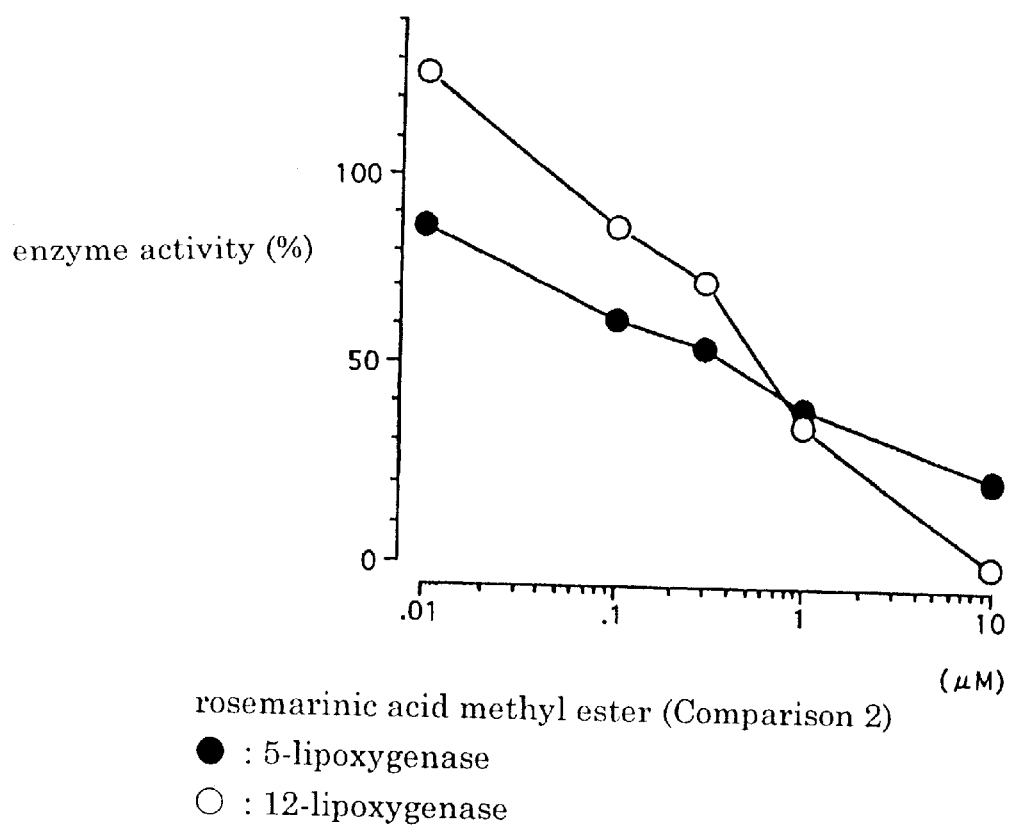
rosemarinic acid methyl ester (Comparison 2)
● : 5-lipoxygenase
○ : 12-lipoxygenase

INHIBITORS OF LIPOXYGENASE

FIELD OF THE INVENTION

This invention relates to inhibitors of lipoxygenase.

BACKGROUND OF THE INVENTION

Technology of the Invention

This invention, in regard to inhibitors of lipoxygenase, is intended for application in medicines regulating or preventing allergic diseases, inflammatory responses or the like. It is intended for use in connection with non-medical supplies, such as cosmetics or food additives and so forth.

Earlier Development

Arachidonic acid, an essential fatty acid, exists inside the body as one compound of cell walls. Once arachidonic acid is stimulated, it is separated from phospholipid by the action of phospholipase. The separated arachidonic acid is metabolized by arachidonic acid metabolic enzymes e.g. lipoxygenase, then changed to substances such as prostaglandin (PG) which is associated with inflammatory responses or the like, *thromboxane (TX) which is associated with the formation of thrombus, and leukotriene (LT) and *lipoxyne, which induce allergic reactions. (See FIG. 1).

Thus, arachidonic acid metabolic enzymes create substances which are the source of compounds that are associated with circulatory and allergic diseases, inflammation and so forth. Therefore, in order to regulate or prevent these diseases, it may be effective to inhibit the metabolism of arachidonic acid by enzyme action.

Some typical enzymes relating to the metabolism of arachidonic acid are 5-lipoxygenase, 12-lipoxygenase, and cyclooxynase (COX). 5-Lipoxygenase metabolizes arachidonic acid into 5-hydroxy-6,8,10,14-eicosatetraenoic acid (5-HETE), and induces the formation of leukotriene (LT) which is associated with allergic diseases, inflammatory responses and asthma. Also, 12-lipoxygenase is an enzyme having an arachidonic acid radical that metabolizes into 12-hydroxy-5,8,10,14-eicosatetraenoic acid (12-HETE). This compound is associated with arteriosclerosis, allergic diseases and metastasis of cancer.

Caffeic acid and quercetine or the like are well recognized as natural inhibitors of lipoxygenase. These substances, however, have not come into practical use as enzyme inhibitors. On the other hand, it is known that very few substances show significant inhibitory activity against 12-lipoxygenase. Other polyphenol group members are natural inhibitors of the activity of lipoxygenase. However, the inhibitory activity of these materials is not sufficient to produce satisfactory results in alleviating disease conditions. Further, it is difficult to cost-effectively purify enzyme inhibitors from natural substances.

Perilla (frutescens) seed is a year-round plant belonging to the perilla (crispa) family. It is indigenous to East Asia and is classified as an oil crop. Perilla (crispa) typically has a square-shaped stem, oval-shaped opposed leaves and small white flowers that bloom in the summer season. Its seeds are a little larger than those of perilla (crispa) and are harvested in the autumn.

Oil obtained from perilla (frutescens) seed is known as perilla oil, and is used as an ingredient in food or paint. Also, oil cake is used as fertilizer or feed. It has already been reported that perilla leaves contain physiologically active substances, however, there have been few studies of perilla (frutescens) seed.

As the result of investigations of rosemarinic acid and its methyl ester carried out by the inventors, from among the five substances that inhibit the enzyme activity of lipoxygenase, i.e.: luteolin, chrysoeriol, rosemarinic acid, rosemarinic acid methyl ester, and apigenin contained in perilla (frutescens) seed, it was found that Japanese Published Examined Patent Application No. 1-121217 has already described the inhibitory activity against 5-lipoxygenase associated with rosemarinic acid or its derivative extracted from fresh leaves of perilla (crispa) family.

Also, Japanese Published Examined Patent Application No. 8-510735 describes the inhibitory activity of apigenin on 5-lipoxygenase.

OBJECTS OF THE INVENTION

An imporantant object of this invention is to provide means to significantly inhibit the activities of 5-lipoxygenase and 12-lipoxygenase in relation to the metabolism of arachidonic acid.

Another object of this invention is to extract active inhibitors of lipoxygenase from natural substances that may be used to regulate and prevent allergic diseases, inflammatory responses, circulatory diseases and metastasis of cancer.

Other and additional objects of this invention will become apparent from a consideration of this entire specification, including the drawings hereof and the claims appended hereto.

BRIEF DESCRIPTION OF THE INVENTION

In accord with and fulfilling these objects, one aspect of this invention is the use of luteolin as an active compound to inhibit the enzyme action of lipoxygenase.

Another feature of this invention is the use of chrysoeriol as an active compound to inhibit the enzyme action of lipoxygenase.

Still another feature of this invention is the compounding of inhibitors of lipoxygenase from alcoholic extracts of perilla (frutescens) seed. These extracts comprise one or more compounds from among luteolin, chrysoeriol, rosemarinic acid, rosemarinic acid methyl ester and apigenin.

A further feature of this invention is that inhibitors of the enzyme action of lipoxygenase can be prepared from the alcoholic extract of perilla (frutescens) seed, including one or more compounds from among luteolin, chrysoeriol, rosemarinic acid, rosemarinic acid methyl ester, and apigenin. This alcoholic extract is suitably subjected to partition by ethyl acetate and water (two layers) and the fraction that partitions to the ethyl acetate layer is the desirable inhibitory fraction.

It may be preferable to use defatted perilla (frutescens) seed in place of the aforementioned untreated perilla (frutescens) seed. It is also possible to use perilla (crispa) seed in place of the aforementioned perilla (frutescens) seed.

The inventors have carried out various experiments on extracts of perilla (frutescens) seed, and have thereby discovered that an ethanol extract of perilla (frutescens) seed has a strong inhibitory effect against the enzyme action of 5-lipoxygenase and 12-lipoxygenase. As a result of a close study, the inventors have discovered that the luteolin, chrysoeriol, rosemarinic acid, rosemarinic acid methyl ester and/or apigenin in an alcoholic extract of perilla (frutescens) seed strongly inhibit lipoxygenase enzyme activity. It was found that luteolin especially has an outstanding inhibitory activity against lipoxygenase. The outstanding inhibitory activity of luteolin on lipoxygenase, together with the lesser inhibitory activity of chrysoeriol, has only come to light through the research of these investigations.

The inventors have also found, through various experiments on seeds of other varieties of perilla (crispa) belonging to the same family as perilla (frutescens), that alcoholic extracts of other seeds also contain substances that effectively inhibit the enzyme activity of lipoxygenase, i.e. luteolin, chrysoeriol. rosemarinic acid and rosemarinic acid methyl ester.

The structural formula of luteolin is as follows (Formula 1)

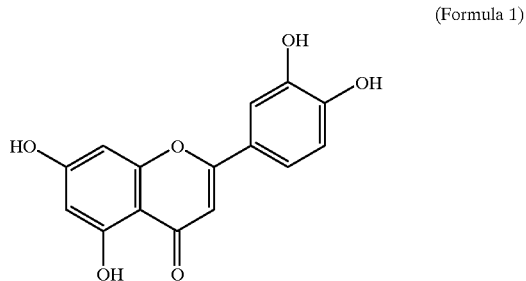

It is known that luteolin exists as a glycoside generally in the bean family i.e. digitalis, etc. Also, it is known that luteolin has physiological activity as an anti-oxidant, a hyaluronidase inhibitor, and so forth.

According to this invention, when using luteolin as an active compound for its lipoxygenase inhibitory activity, it can be extracted or purified from the rind of citrus fruits as well as from perilla (frutescens) seed or perilla (crispa) seed and leaves. However, in industrial production, it may be preferable to use perilla (frutescens) seed or perilla (crispa) seed since the leaves contain only small amounts of luteolin.

The structural formula of chrysoeriol is as follows:

(Formula 2)

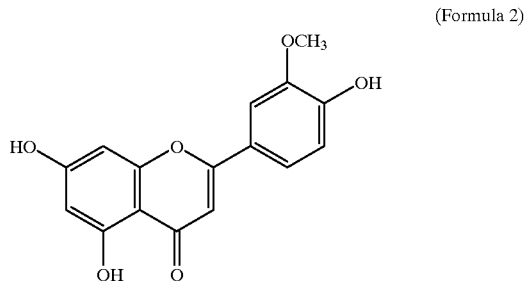

There are only a few reports of chrysoeriol having physiological activity as an anti-cancer agent or antibiotic. According to this invention, in order to use chrysoeriol as an active compound for its lipoxygenase inhibitory activity, it can be extracted or purified from perilla (frutescens) seed or perilla (crispa) seed and leaves.

It is preferable to use ethanol as solvent/extractant for the extraction of luteolin and chrysoeriol from perilla (frutescens) seed and perilla (crispa) seed. As well as efficiently extracting the effective substances, the use of ethanol allows the extracts to be available in formulations that are useful for both internal and external application. However, when the extract is to be used for external application only, ethyl acetate, acetone, methanol, butanol and so forth can also be used as the extractant.

In the extraction of the chrysoeriol, or luteolin from perilla seed or leaves, as the case may be, it is preferable to use an alcohol concentration between about 70 and 85% (v/v). If the concentration is less than about 70% (v/v), effective substances will not be sufficiently extracted, and if concentration is greater than about 85% (v/v), perilla (frutescens) seed oil easily dissolves into the alcohol. In order to improve the extraction of the active compound from seed, it is preferable to use repeated alcoholic extractions at various levels of concentration.

Inhibitory substances obtained by alcoholic extraction of perilla (frutescens) seed and perilla (crispa) seed normally contain luteolin, chrysoeriol, rosemarinic acid, rosemarinic acid methyl ester and apigenin. It is possible that, under different conditions of extraction, some or any of these substances may not be recovered. However, recovery of at least one of these substances is sufficient to inhibit the effects of lipooxygenase.

The reason why alcoholic extracts of perilla (frutescens) seed or perilla (crispa) seed are best partitioned by ethyl acetate and water is that such a subsequent extraction produces a higher concentration of the active compound. A high concentration of luteolin, chrysoeriol, rosemarinic acid, rosemarinic acid methyl ester concentrates in the layer of ethyl acetate, while non-active compounds such as glycoside, etc., gather in the water layer. Therefore, the active compound can be more efficiently concentrated by using ethyl acetate to capture these effective compounds.

It is possible make inhibiting compositions by directly compounding the aforementioned alcoholic extract and ethyl acetate partitioned compounds as inhibitors of the enzyme activity of lipoxygenase. However it may also be possible to isolate the active compound contained in these extracts. When isolating luteolin, for example, the ethyl acetate layer that contains the luteolin can be subjected to silica gel column chromatography (chloroform:methanol= 10:1) and the most active fraction (that is the fraction with the highest concentration of luteolin) is collected. The luteolin can then be separated as an insoluble fraction from the mixed solvent (for example: chloroform:methanol= 15:1).

In this invention, alcoholic extraction using defatted perilla (frutescens) seed and perilla (crispa) seed provides a high concentration of active compounds. If the fat of the perilla (frutescens) seed and of the perilla (crispa) seed is extracted by treatment with organic solvents, the extracted oil contains only a small amount of physiologically active compounds, such as luteolin and chrysoeriol, because these active compounds are concentrated in the defatted fraction.

Hexane, for example, is appropriate as an organic solvent for defatting these seeds because the thus extracted oil can be used for food. In fact, the entire extract, oil and hexane or the like, from defatted perilla (frutescens) seed can also be used as an ingredient of foods and so forth. In the case where the substance extracted from defatted perilla (frutescens) seed is to be used for external application only, it would be possible to use not only hexane but also other non-polar solvent. According to this invention, inhibitors of the enzyme activity of lipoxygenase may be used in medical and non-medical applications. Exemplary non-medical applications include, among others: cosmetics, ingredient of foods and so forth. Since inhibitors of lipoxygenase, as described in this invention, exhibit effective inhibitory activity against the role of lipoxygenase in allergy and inflammation, it will also be appropriate to use them in anti-allergic or anti-inflammatory drugs or medicines.

In this invention, inhibitors of the enzyme activity of lipoxygenase may be administered either orally or by other means, such as topically. In the case of oral administration, they can be given in tablet, granule, small grain, or powder form. In the case of non-oral administration, inhibitors of lipoxygenase can be given by injection, intravenous drip, as solid, in suspension, in a viscoelastic fluid i.e. as a suppository that can be absorbed through the mucous membrane, by local topical application to internal or external organic tissue, or by other external administration i.e. intradermal, hypodermic, intramascular and intravenous injection, local topical application, spray, suppository, or injection to the bladder and so forth.

The dose to be administered may fluctuate in accordance with administrative method, seriousness of the condition, age of the patient, condition and general situation of disease, stage of disease and so on. Normally, adults can take about 0.5 to 5,000 mg of active compound a day and children preferably can take about 0.5 to 3,000 mg of active compound a day.

The concentration of inhibitors of lipoxygenase can be varied according to the type of administration. In case of oral administration or absorption through the mucous membrane, the concentration can be approximately 0.3 to 15.0wt %, and in case of non-oral administration, it can be approximately 0.01 to 10 wt %. It should be understood that the above mentioned amount is only exemplary and it is within the scope of this invention to vary the concentration and dosage in accordance with prevailing conditions.

When the inhibitors of lipoxygenase of this invention are to be used for medical or non-medical supplies or cosmetics, they may be used together with various common components of these formulations. These conventional ingredients are exemplified by:

Oils: animal oil, vegetable oil, mineral oil, ester oil, wax oil, silicon oil, higher alcohols, phospholipid, fatty acids, etc.

Surface active agents: anionic, cationic, amphoteric or non-ionic surface active agent Vitamins: vitamin A, vitamin B, folic acid, nicotinic acid, pantothenic acid, biotin, vitamin C, vitamin D, vitamin E, ferulic acid, γ-orizanol etc.

Ultraviolet absorbents: p-aminobenzoic acid, anthranil, salicylic acid, coumrin, benzotriazol, tetrazol, imidazoline, purimidine, dioxane, furan, pyrone, camphor, nucleic acid, allantoin and their conductors, amino acid compound, siconin, baicalin, baicalein, berberine, etc.

Anti-oxidants: ester stearate, nordihydroguaseleten acid, dibutyl hydroxytoluene, butyl hydroxyanisole, para hydroxyanisole, gallic acid propyl ester, sesamol, sesamolin, gossypol, etc.

Thickeners: hydxyethyl cellulose, ethyl cellulose, carboxyethyl cellulose, methyl cellulose, carboxymethyl cellulose, carboxyethyl cellulose, sodium, hydroxypropyl cellulose, nitrocellulose, polyvinyl alcohol (PVA), polyvinyl alcohol methyl ether, polyvinyl pyrrolidone, polyvinyl methacrylate, polyacrylic acid, carboxyvinyl polymer, gum arabic, tragacanth gum, agar-agar, casein, gelatin, pectin, starch, alginic acid and its salts.

Moisture retention agents: propylene glycol, 1,3 butylene glycol, polyethylene glycol, glycerol, chondroitin sulfate, hyaluronic acid, sodium lactate, etc.

Others: lower alcohols, polyhydric alcohols, water-soluble polymers, pH regulators, antiseptics/preservatives, coloring agents, perfumes, refrigerants, stabilizers, animal and vegetable extracts, animal and vegetable proteins, animal and vegetable polysaccharides, animal and vegetable glycoproteins and their decomposition products, metabolites of incubated microorganisms, blood circulation promoters, other anti-inflammatory agents, cell fraction agent amino acids, and their salts, horn-like material dissolution agent, astringents, wound dressing materials, foam fillers, oral agents, deodorants and the like.

The above mentioned materials can be used in medical or non-medical supplies such as cream, ointment, face lotion, body lotion, milky lotion, pack, oil, soap, including medicated soap, cleansing soap, bath aromatics, shampoo, hair conditioner, sprays. Also, they can be used in sanitary products, non-woven fabrics that are useful for tissues, wet wipes and the like, composites for oral use in case of stomatitis and so forth.

In the case where lipoxygenase inhibitors as described in this invention are to be used in food additives, they can be also used in general foodstuffs such as confectionery, noodles, soup, beverages, and health foods including nutritional supplements. For example, inhibitors of lipoxygenase enzyme activity can be used together with powdered cellulose, and can be spray dried or freeze-dried. Such a powder, granule, tablets or solution can easily be mixed with foods.

EFFECTIVENESS OF THE INVENTION

5-HETE, which is a metabolite of 5-lipoxygenase, produces leukotriene and thereby induces allergic reactions or inflammatory responses. 12-HETE, which is metabolite of arachidonic acid by the action of 12-lipoxygenase, is known to be a physiologically active substance in regard to arteriosclerosis or metastasis of cancer, Therefore, it is possible to regulate or prevent allergic diseases, inflammatory responses, circulatory diseases, metastasis of cancer, or the like by inhibiting these substances selectively.

As described above, according to this invention, it is possible to extract substances that have significant lipoxygenase enzyme action inhibition from natural substances such as perilla (frutescens) seed and other similar materials such that these may be used in food additives in order to effectively regulate allergic reactions and inflammatory responses.

Furthermore, as described herein, inhibitors of lipoxygenase can be obtained from defatted perilla after perilla (frutescens) seed oil for food has been collected. This means that defatted perilla (frutescens) seed can provide another resource.

This invention provides active inhibitors of the enzyme activity of lipoxygenase. These inhibitors are obtained from natural substances and have significant inhibitory activities against both 5-lipoxygenase and 12-lipoxygenase. These inhibitors are available to regulate or prevent allergic reactions, inflammatory responses, circulatory problems and metastasis of cancer. A feature of the lipoxygenase inhibitors as described in this invention is that at least one of luteolin or chrysoeriol are used as the active compound.

Another feature of this invention is that lipoxygenase inhibitors of this invention is the recovery thereof from alcoholic extract of perilla (frutescens) seed containing one or more compounds from among luteolin, chrysoeriol, rosemarinic acid, rosemarinic acid methyl ester and apigenin. A further feature is that the aforementioned alcoholic extract is partitioned with ethyl acetate and water, and especially effective inhibitors are obtained from the ethyl acetate layer. Defatted perilla (frutescens) seed may preferably be substituted for whole perilla (frutescens) seed. Perilla (crispa) seed can be substituted for or used with the aforementioned perilla (frutescens) seed.

BRIEF DESCRIPTION OF THE DRAWING

FIG. 2 is a flow chart to describe the method for isolation of inhibitors of lipoxygenase in accordance with the examples in this invention.

FIG. 3 shows the correlation between the concentration of isolated luteolin and inhibition of 5-lipoxygenase and 12-lipoxygenase in accordance with the embodiments in this invention.

FIG. 4 shows the correlation between the concentration of isolated chrysoeriol and inhibition of 5-lipoxygenase and 12-lipoxygenase in accordance with the embodiments of this invention.

FIG. 5 shows the correlation between the concentration of ethanolic extraction and ethyl acetate fraction, and the inhibition of 5-lipoxygenase in accordance with the embodiments in this invention.

FIG. 6 shows the correlation between the concentration of ethanolic extraction and ethyl acetate fraction, and the inhibition of 12-lipoxygenase in accordance with the embodiments in this invention.

FIG. 7 shows the correlation between the concentration of isolated rosemarinic acid and the inhibition of 5-lipoxygenase and 12-lipoxygenase in accordance with the comparisons in this invention.

FIG. 8 shows the correlation between the concentration of isolated rosemarinic acid methyl ester and the inhibition of 5-lipoxygenase and 12-lipoxygenase in accordance with the comparisons in this invention.

DETAILED DESCRIPTION OF THE PREFERRED EMBODIMENTS

Isolation of Lipoxygenase Inhibitors

Figure 1:
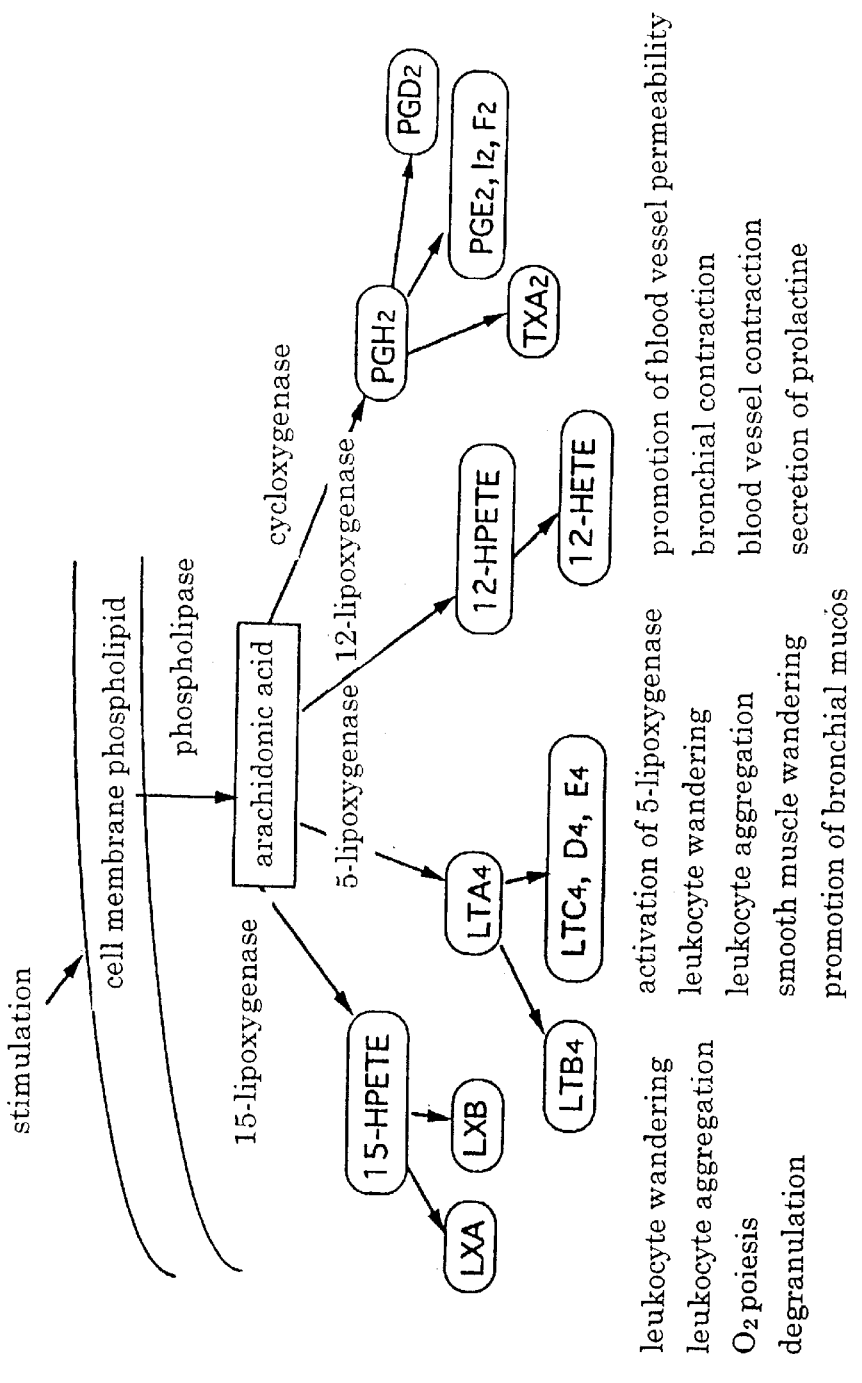
FIG. 1 shows the physiological action of arachidonic acid metabolic enzyme.

As described in FIG. 2, crushed perilla (frutescens) seed was extracted (defatted) with hexane, and, after separation of the fat fraction, the residue of defatted perilla (frutescens) seed was then extracted by refluxing with 80% aqueous ethanol. The concentrated ethanolic extract was partitioned by hexane and 80% aqueous methanol. The 80% aqueous methanolic layer was evaporated to dryness and then partitioned between ethyl acetate and water. After separating the ethyl acetate layer from the water layer, some of the ethyl acetate solvent was distilled off, and a fraction of product in a smaller quantity of ethyl acetate was thus obtained.

The remaining ethyl acetate fraction was subjected to silica gel column chromatography (using a solvent comprising chloroform:methanol=10:1) to give further separate fractions.

Fraction 1 was suspended in the mixed solvent (chloroform:methanol=20:1) to isolate chrysoeriol as an insoluble fraction.

Fraction 2 was suspended in the mixed solvent (chloroform:methanol=15:1) to isolate luteolin as an insoluble fraction.

The pure luteolin and pure chrysoeriol isolated from perilla (frutescens) seed in this manner are respectively designated Embodiment 1 and 2.

The ethanolic extraction (as illustrated in FIG. 2) obtained by evaporation of solvent was designated Embodiment 3, and the ethyl acetate layer obtained by partitioning the ethanolic extraction fraction was evaporated with the solvent, and then the fraction in the ethyl acetate was designated Embodiment 4.

Test of 5-Lipoxygenase Inhibitory Activity

A test of the substances' effectiveness as inhibitors of 5-lipoxygenase was conducted for the above mentioned Embodiment 1 to 4.

(1) Formation of Enzyme Solution of 5-Lipoxygenase

Peritoneal polymorphonuclear leukocytes (PMNL) were prepared from normal Wistar-King rats (150–400 g) injected intraperitoneally with 5% (w/v) glycogen (20 mL/kg). A suspension in potassium phosphate buffer (50 mM, pH 7.4) was homogenized and centrifuged. The supernatant was used as the enzyme solution of 5-lipoxygenase.

(2) Measurement of Inhibitory Activity Against 5-Lipoxygenase

Four to six testing solutions with different levels of concentrations were prepared for Embodiments 1 to 4. 0.02 mL Of enzyme solution (2 mg protein/mL) and [11-$^{14}$C] arachidonic acid (0.05 Ci) were incubated with each testing solution (0.02 mL) and $Ca^{2+}$ and ATP at 37° C. for 5 min.

After incubation at 37° C. for 5 min, the reaction was terminated by adding 0.2 mL of 0.5 N formic acid, and the metabolite was extracted by 3 mL of ethyl acetate.

Then the extracted solution was subjected to thin-layer chromatography (TLC) and developed with ether/petroleum ether/acetic acid (50:50:1, v/v) at 4° C. The radioactive metabolites generated by 5-lipoxygenase were detected and quantified using autoradiography. The inhibitory activity on 5-lipoxygenase was measured and expressed as a percentage of the control.

For comparison, inhibition of 5-lipoxygenase activity was measured in the same manner, for rosemarinic acid (Comparison 1) obtained by purifying fraction 3 as indicated in FIG. 2, rosemarinic acid methyl ester (Comparison 2), hexane fraction (Comparison 3) obtained by evaporating hexane layer with solvent, and water fraction (Comparison 4) obtained by evaporating the water layer also with the solvent. The results are shown in FIGS. 3 to 5, 7 and 8.

As a result, Embodiments 1 to 4 showed significant inhibitory activities against 5-lipoxygenase. Embodiment 1 (luteolin) especially, as indicated in FIG. 3, showed a stronger inhibitory activity than that of Comparison 1 (rosemarinic acid) and Comparison 2 (rosemarinic acid methyl ester) which had already been reported to have 5-lipoxygenase inhibitory action.

Embodiment 4 (ethyl acetate fraction) showed even more significant inhibitory activity than that of Embodiment 3 (ethanolic extraction). The reason for this phenomenon seems to be that active compounds are concentrated in the ethyl acetate layer by eliminating less active water and oil soluble substances from the ethanolic extract. Also, the inhibitory activities of Embodiment 3 (ethanolic extraction) and 4 (ethyl acetate fraction) seem to be correlated with their luteolin content.

Table 1 shows the $IC_{50}$ values for inhibition of lipoxygenase activities for Embodiment 1 (luteolin), 2 (chrysoeriol), Comparison 1 (rosemarinic acid) and Comparison 2 (rosemarinic acid methyl ester), together with Comparison 5 (caffeic acid) and 6 (quercetin) measured in the same manner.

TABLE 1

$IC_{50}$ Values for Inhibition of 5-Lipoxygenase Activity by Phenolic Compounds

| Classification | Compound | $IC_{50}$ (M) 5-LO |
|---|---|---|
| Embodiment 1 | luteolin | 0.1 |
| Embodiment 2 | chrysoeriol | 22.0 |
| Comparison 1 | rosemarinic acid | 6.2 |
| Comparison 2 | rosemarinic acid methyl ester | 0.6 |
| Comparison 5 | caffeic acid | 72.0 |
| Comparison 6 | quercetin | 0.2 |

As shown by the comparative data reported in Table 1, the $IC_{50}$ value of Embodiment 1 (lutelion) is 0.1 M which is very much higher than that of the other compounds, and showed a significant 5-LO inhibitory activity.

Test of 12-Lipoxygenase Inhibitory Activity

A test of the substances' effectiveness as inhibitors of the enzyme activity of 12-lipoxygenase was conducted for Embodiment 1 to 4.

(1) Formation of Enzyme Solution of 12-Lipoxygenase

Blood was collected from normal Wistar-King rats (150–400 g) and 0.5 mM of EDTA was added as anticoagulant. The centrifuged supernatant (1,200 rpm for 10 min.) was again centrifuged at 3,000 rpm for 10 min. The deposited platelets were washed by 25 mM Tris/HCl buffer (pH 7.4) 1 mM EDTA /130 mM NaCl. The suspension of platelets in 1 mM EDTA was homogenized and used as an enzyme solution of 12-lipoxygenase.

(2) Measurement of Inhibitory Activity of 12-Lipoxygenase

Four to six testing solutions with different levels of concentration were prepared for Embodiment 1 to 4. 0.13 mL of enzyme solution (2 mg protein/mL) and $[1-^{14}C]$ arachidonic acid (0.05 Ci) were incubated with a testing solution (0.02 mL) at 37° C. for 5 min.

After incubation at 37° C. for 5 min., the reaction was terminated by adding 0.2 mL of 0.5 N formic acid, and the metabolite was extracted by adding 3 mL of ethyl acetate. Then, the extracted substances were subjected to thin-layer chromatography (TLC) and developed with chloroform/methanol/acetic acid/water (90:8:1:0.8, v/v). The radioactive metabolites of 12 lipoxygenase were detected and quantified using autoradiography. The inhibitory activity of 12-lipoxygenase was measured and expressed as a percentage of the control.

As a comparison, inhibition of 12-lipoxygenase enzyme activity was measured in the same manner, for rosemarinic acid (Comparison 1) obtained by purifying fraction 3 as indicated in FIG. 2, rosemarinic acid methyl ester (Comparison 2), hexane fraction (Comparison 3) obtained by evaporating hexane layer with solvent, and water fraction (Comparison 4) obtained by evaporating water layer also with solvent. The results are shown in FIGS. 3, 4 and 6 to 8.

As shown, Embodiments 1 to 4 had significant inhibitory activities against 12-lipoxygenase. Embodiment 1 (luteolin) was especially effective, as indicated in FIG. 3. It showed a very strong inhibitory activity, similar to that against 5-lipoxygenase.

Embodiment 4 (ethyl acetate fraction) as indicated in FIG. 6, showed a stronger inhibitory activity than Embodiment 3 (ethanolic extraction), again probably because the active compounds of ethanolic extract were concentrated in the ethyl acetate layer.

Test for Regulating Inflammatory Reaction Against TPA-Induced Inflammation to the Ears of Mice As described in this section, a test for regulating action against TPA-induced inflammation to the ears of mice was conducted.

(1) Application to the Skin

Test solutions for Embodiment 1, 3 and 4 were prepared and applied to the right ears of mice (ICR, 5 weeks old, Clair) by adding acetone solution of TPA (0.8 μg/20 μl/ear). After 4 hours, the weights of the right and left ears were measured to give the expansion coefficient of dropsical swelling on the right ear against the left ear. The regulating coefficient of inflammation against mice in a control group was also measured. 'Control' herein means that the same test was also conducted on a group without applying samples of test solutions under the same condition.

Also, as a comparison, data on NDGA (Comparison 7) which has already been reported, are listed in Table 2.

TABLE 2

| Class. | Compound | Application | Amount | Regulating Coefficient(%) |
|---|---|---|---|---|
| Embodiment 1 | luteolin | skin | 0.15 mg/ear | 85 |
| Embodiment 1 | luteolin | skin | 0.3 mg/ear | 100 |
| Embodiment 3 | ethanolic extraction | skin | 0.5 mg/ear | 25 |
| Embodiment 4 | ethyl acetate fraction | skin | 1.0 mg/ear | 45 |
| Comparison 7 | NDGA | skin | 0.5 mg/ear | 40 |
| Embodiment 4 | ethanolic extraction | oral | 1.0% mixed w/food | 20 |

Note: Comparison 7
Source: "I-1 Evaluation of anti-inflammatory medicine and anti-allergic medicine by animal experiment" of "Vol. 12 - Inflammation and Allergy" compiled by Prof. Kazuo Ouchi, Pharmaceutical Department of Tohoku Univ. & Published by Hirokawa Shoten As indicated in Table 2, luteolin (0.3 mg/ear) of Embodiment 1, regulated TPA-induced inflammation on the ear by 100%, Embodiment 3 (ethanolic extraction: 0.5 mg/ear) gave 25% reduction, and Embodiment 4 (ethyl acetate fraction: 1.0 mg/ear) gave 45% reduction, while using the Regulating coefficient of Comparison 7 (NDGA: 0.5 mg/ear) as the substance for inhibition of the enzyme activity of 5-lipoxygenase gave 40% reduction. In other words, Embodiments 1, 3 and 4 had a significant regulating effect against inflammation. Also, Embodiment 1 showed an anti-inflammatory action, which correlated with the concentration of luteolin.

(2) Oral Application

As a sample, 5 g of food containing 1% of Embodiment 4 (ethanolic extraction) was given to the mice for 4 weeks, then TPA acetone solution (0.8 μg/20 μl/ear) was applied to the right ears of mice (I.C.R, 5 weeks old/Clair). After 4 hours, the weights of the right and left ears were respectively measured to give the expansion coefficient of inflammation on the right ear against the left ear together with the regulating coefficient of inflammation against mice in a control group. 'Control' herein means that the test was conducted on a group without applying samples under the same conditions. The results are shown in Table 2.

As indicated in Table 2, the regulating coefficient of Embodiment 4 (ethanolic extraction: 1% with food) against inflammation was 20%, and oral application also provided a significant anti-inflammatory action. No increases or decreases in weight were found in comparison with the control group.

Allergy Control Test Against Oxazolone-Induced Inflammation in the Ears of Mice

As described in this section, an allergy control test of oxazolone-induced inflammation to the ears of mice was conducted.

(1) Application to the Skin

Oxazolone solution in ethanol (500 μg/100 μl) was applied to the abdominal region of mice (I.C.R, 5 weeks old, Clair), that had been shaved by hair clippers under an anesthetic of Nembutal (Immunization).

After 5 days of immunization, oxazolone solution in acetone, containing a prescribed amount of the sample being tested (Embodiment 1), was applied to the right ears of the mice (Challenge). After 48 hours, the weights of the right and left ears were measured to give the expansion coefficient of inflammation on the right ear against the left ear. The regulating coefficient of inflammation against mice in a control group was also measured. 'Control' herein means that the test was also conducted on a group without applying samples under the same conditions.

Also, as a comparison, data on NDGA (Comparison 7), ketoprophen (Comparison 8), phenidone (Comparison 9) and mepiramine (Comparison 10) which had already been reported, were listed in Table 3.

TABLE 3

| Class. | Compound | Application | Amount | Regulating Coefficient(%) |
|---|---|---|---|---|
| Embodiment 1 | luteolin | skin | 0.3 mg/ear | 52 |
| Comparison 7 | NDGA | skin | 1.0 mg/ear | 38 |
| Comparison 8 | ketoprophene | skin | 1.0 mg/ear | 32 |
| Comparison 9 | phenidone | skin | 1.0 mg/ear | 44 |
| Comparison 10 | mepiramin | skin | 1.0 mg/ear | 38 |
| Embodiment 3 | ethanolic extraction | oral | 1.0% mixed w/food | 34 |

Note: Comparison 7 to 10
Source: "I-1 Evaluation of anti-inflammatory medicine and anti-allergic medicine by animal experiment" of "Vol. 12 - Inflammation and Allergy" compiled by Prof. Kazuo Ouchi, Pharmaceutical Department of Tohoku Univ. & Published by Hirokawa Shoten As indicated in Table 3, Embodiment 1 showed a higher regulating coefficient for a smaller amount of application against Comparisons 7 to 10. In other words, luteolin as an active compound has a significant anti-allergic action.

(2) Oral Application

From the beginning of the application until when the weights of ears were measured, 5 g of food mixed with 1% of sample (Embodiment 3) was given to the mice every day. On the 8th day from the beginning of application, immunization was applied to the shaved abdominal region of the mice by an ethanol solution of oxazolone. After 5 days, a solution of oxazolone in acetone was applied to the right ears of the mice (Challenge). After 48 hours, the weights of the right and left ears were measured to give the expansion coefficient of inflammation on the right ear against the left ear. The regulating coefficient of inflammation against mice in a control group was also measured. 'Control' herein means that the test was conducted on a group without applying samples under the same conditions. The results are shown in Table 4.

As indicated in Table 4, Embodiment 3 (ethanolic extraction: 1% mixed with food) regulated oxazolone-induced inflammation on the ear by 34%. In other words, oral application also provided a significant anti-allergic action. No increases or decreases in weight of mice in Embodiment 3 was found compared with that of the control group.

What is claimed is:

1. A composition comprising a sufficient amount of an ethanol extract of perilla seed, comprising at least one compound selected from the group consisting of luteolin, chrysoeriol, rosemarinic acid, rosemarinic acid methyl ester and apigenin, effective to inhibit the enzyme action of lipoxygenase.

2. The composition as claimed in claim 1 wherein said ethanol extract is derived from defatted perilla (crispa) seed.

3. A method of combating an allergic reaction and inflammatory responses which comprises administering, to an animal having an allergic reaction, an inhibitor of the enzyme action of lipoxygenase comprising a composition as claimed in claim 1.

4. A method of combating an allergic reaction and inflammatory responses as claimed in claim 3 wherein said composition comprises luteolin.

5. A method of combating an allergic reaction and inflammatory responses as claimed in claim 3 wherein said composition comprises chrysoeriol.

6. A comestible comprising the composition claimed in claim 1.

7. A cosmetic comprising the composition claimed in claim 1.

8. A method of combating allergic reaction and inflammatory responses which comprises administering, to an animal having an allergic reaction, an inhibitor of the enzyme action of lipoxygenase comprising an ethanol extract of perilla seed, comprising an amount of at least one compound selected from the group consisting of luteolin, chrysoeriol, rosemarinic acid, rosemarinic acid methyl ester and apigenin, effective to inhibit the enzyme action of lipoxygenase.

9. The method of combating allergic reaction and inflammatory responses as claimed in claim 8 wherein said ethanol extract is derived from the species perilla (frutescens) seed.

10. The method of combating allergic reaction and inflammatory responses as claimed in claim 5 wherein said ethanol extract is derived from the species perilla (crispa) seed.

11. The method of combating allergic reaction and inflammatory responses as claimed in claim 5 wherein said ethanol extract is derived from defatted species perilla (crispa) seed.

12. A method of combating allergic reaction and inflammatory responses which comprises administering, to an animal having an allergic reaction, an inhibitor of the enzyme action of lipoxygenase comprising an ethyl acetate extract of perilla seeds comprising an amount of at least one compound selected from the group consisting of luteolin, chrysoeriol, rosemarinic acid, rosemarinic acid methyl ester and apigenin, effective to inhibit the enzyme action of lipoxygenase.

13. The method of combating allergic reaction and inflammatory responses as claimed in claim 12 wherein said ethyl acetate extract is derived from the species perilla (frutescens) seed.

14. The method of combating allergic reaction and inflammatory responses as claimed in claim 12 wherein said ethyl acetate extract is derived from the species perilla (crispa) seed.

15. The method of combating allergic reaction and inflammatory responses as claimed in claim 12 wherein said ethyl acetate extract is derived from defatted species perilla (crispa) seed.

16. A method of inhibiting the enzyme action of lipoxygenase that comprises administering to an animal in need thereof an effective amount of an ethanol or ethyl acetate extract of perilla seed comprising at least luteolin and chrysoeriol.

17. A composition comprising an ethanol extract of perilla seed.

18. The composition as claimed in claim 17 comprising luteolin.

19. The composition as claimed in claim 18 wherein said perilla seed comprises perilla (frutescens) seed.

20. The composition as claimed in claim 18 wherein said perilla seed comprises perilla (crispa) seed.

21. The composition as claimed in claim 17 comprising chrysoeriol.

22. The composition as claimed in claim 19 wherein said perilla seed comprises perilla (frutescens) seed.

23. The composition as claimed in claim 19 wherein said perilla seed comprises perilla (crispa) seed.

24. A pharmaceutical composition comprising a composition as claimed in claim 17 admixed with a pharmaceutically acceptable carrier.

* * * * *